United States Patent
Takami et al.

(10) Patent No.: US 9,835,702 B2
(45) Date of Patent: Dec. 5, 2017

(54) MAGNETIC RESONANCE IMAGING APPARATUS, MAGNETIC FIELD ADJUSTMENT IMPLEMENT FOR MAGNETIC RESONANCE IMAGING APPARATUS, MAGNETIC RESONANCE IMAGING METHOD, AND METHOD OF ADJUSTING MAGNETIC FIELD FOR MAGNETIC RESONANCE IMAGING APPARATUS

(71) Applicant: TOSHIBA MEDICAL SYSTEMS CORPORATION, Otawara-Shi, Tochigi (JP)

(72) Inventors: Shohei Takami, Yokohama (JP); Yoshitomo Sakakura, Nasushiobara (JP); Kazuto Nogami, Nasushiobara (JP); Hidekazu Tanaka, Otawara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1271 days.

(21) Appl. No.: 13/766,831

(22) Filed: Feb. 14, 2013

(65) Prior Publication Data
US 2013/0154636 A1 Jun. 20, 2013

Related U.S. Application Data

(63) Continuation of application No. PCT/JP2012/061690, filed on May 7, 2012.

(30) Foreign Application Priority Data

May 10, 2011 (JP) .................................. 2011-105752

(51) Int. Cl.
*G01R 33/421* (2006.01)
*G01R 33/3873* (2006.01)
(Continued)

(52) U.S. Cl.
CPC ....... *G01R 33/421* (2013.01); *G01R 33/3873* (2013.01); *G01R 33/3875* (2013.01); *A61B 5/0046* (2013.01); *A61B 5/055* (2013.01)

(58) Field of Classification Search
CPC .............. G01R 33/421; G01R 33/3873; G01R 33/3875; A61B 5/0046; A61B 5/055
See application file for complete search history.

(56) References Cited

U.S. PATENT DOCUMENTS 4,990,877 A * 2/1991 Benesch ............ G01R 33/3873
324/318
5,313,164 A * 5/1994 Starewicz .............. G01R 33/24
324/318

(Continued)

FOREIGN PATENT DOCUMENTS

CN 101334455 A 12/2008
CN 101957438 A 1/2011
(Continued)

OTHER PUBLICATIONS

Fontius, Joerg, Nuclear magnetic resonance imaging device e.g. for diagnostic medical use, Dec. 1998, Publication No. DE19741748 (machine translation of foreign patent from Espacenet).*

(Continued)

*Primary Examiner* — Dixomara Vargas
(74) *Attorney, Agent, or Firm* — Nixon & Vanderhye P.C.

(57) ABSTRACT

According to one embodiment, a magnetic field adjustment implement for a magnetic resonance imaging apparatus includes a magnetic field adjustment unit and a placing unit. The magnetic field adjustment unit is configured to improve a uniformity of a static magnetic field formed by a magnet of the magnetic resonance imaging apparatus. The static magnetic field is formed under an influence of a circumstance in a shield room in which the magnet is placed. The magnetic field adjustment is placed outside the magnet. The (Continued)

placing unit is configured to place the magnetic field adjustment unit outside the magnet.

17 Claims, 10 Drawing Sheets

(51) Int. Cl.
    *G01R 33/3875*     (2006.01)
    *A61B 5/055*     (2006.01)
    *A61B 5/00*     (2006.01)

(56) References Cited

U.S. PATENT DOCUMENTS

| | | | | |
|---|---|---|---|---|
| 5,361,054 | A * | 11/1994 | Knuttel | G01R 33/3806 324/318 |
| 5,463,364 | A | 10/1995 | Muller | |
| 5,469,123 | A * | 11/1995 | Muller | G01R 33/421 174/385 |
| 5,987,672 | A | 11/1999 | Oosterwaal | |
| 6,748,749 | B2 * | 6/2004 | Tsuda | G01R 33/3815 62/49.2 |
| 6,781,492 | B2 * | 8/2004 | Takeshima | G01R 33/3806 324/319 |
| 6,845,262 | B2 * | 1/2005 | Albert | G01R 33/445 324/307 |
| 6,889,070 | B2 | 5/2005 | Tsuda | |
| 7,417,434 | B2 * | 8/2008 | Overweg | G01R 33/34046 324/318 |
| 8,575,934 | B2 | 11/2013 | Iwasa et al. | |
| 8,836,332 | B2 * | 9/2014 | Shvartsman | G01R 33/421 324/309 |
| 9,664,763 | B2 * | 5/2017 | Amthor | G01R 33/4808 |
| 2007/0279060 | A1 | 12/2007 | Dannels et al. | |

FOREIGN PATENT DOCUMENTS

| | | |
|---|---|---|
| EP | 0 424 600 | 5/1991 |
| JP | 61-55313 | 4/1986 |
| JP | 63-73908 | 5/1988 |
| JP | 2-83904 | 3/1990 |
| JP | 5-39507 | 5/1993 |
| JP | 5-121227 | 5/1993 |
| JP | 11-19061 | 1/1999 |
| JP | 2002-143124 | 5/2002 |
| JP | 2003-135425 | 5/2013 |

OTHER PUBLICATIONS

Notification of Transmittal of Translation of the International Preliminary Report on Patentability in PCT/JP2012/061690 dated Nov. 21, 2013.
Final Office Action dated Sep. 6, 2016 in JP Patent Application No. 2012-106348.
Office Action dated Jun. 17, 2014 in CN Patent Application No. 201280000478.3.
Office Action dated Jan. 19, 2016 in JP Patent Application No. 2012-106348.
International Search Report for PCT/JP2012/061690, dated Jul. 17, 2012.
Non-English Written Opinion for PCT/JP2012/061690 dated Jul. 17, 2012.

* cited by examiner

MAGNETIC RESONANCE IMAGING APPARATUS, MAGNETIC FIELD ADJUSTMENT IMPLEMENT FOR MAGNETIC RESONANCE IMAGING APPARATUS, MAGNETIC RESONANCE IMAGING METHOD, AND METHOD OF ADJUSTING MAGNETIC FIELD FOR MAGNETIC RESONANCE IMAGING APPARATUS

CROSS REFERENCE

This is a continuation of Application PCT/JP2012/61690, filed May 7, 2012.

This application is based upon and claims the benefit of priority from Japanese Patent Application No. 2011-105752, filed May 10, 2011; the entire contents of which are incorporated herein by reference.

FIELD

Embodiments described herein relate generally to a magnetic resonance imaging (MRI) apparatus, a magnetic field adjustment implement for a magnetic resonance imaging apparatus, a magnetic resonance imaging method, and a method of adjusting a magnetic field for a magnetic resonance imaging apparatus.

BACKGROUND

MRI is an imaging method which magnetically excites nuclear spin of an object set in a static magnetic field with a RF (radio frequency) signal having the Larmor frequency and reconstructs an image based on NMR (nuclear magnetic resonance) signals generated due to the excitation.

A static magnetic field magnet included in an MRI apparatus generates a static magnetic field whose intensity is high for imaging. For this reason, in order to avoid magnetic influence on surrounding electronic devices, an MRI apparatus is placed in an imaging room which has a function as a shield room to magnetism.

In a recent MRI apparatus, a super conductive magnet is used as a static magnetic field magnet. Therefore, it is possible to form a high magnetic field more than or equal to 1.5 [T] (tesla) in an imaging space. On the other hand, an old MRI apparatus has a permanent magnet as a static magnetic field magnet and can form a magnetic field more than or equal to 0.3 [T]. A comparatively recent MRI apparatus can form an about 0.8 [T] of magnetic field.

In recent years, the needs of replacing an old type of MRI apparatus, which passed through long years, with a newest MRI apparatus are growing. However, a shield room for an outdated MRI apparatus having a permanent magnet is designed so that a sufficient magnetic shield effect may be gained against a 0.3 [T] to at most 0.8 [T] of magnetic field. For this reason, if an MRI apparatus which forms a high magnetic field of 1.5 [T] and above is placed in a conventional and narrow shield room as it is, a problem of non-negligible magnetic field leak from the shield room arises.

In order to solve this problem, ingenuity for placing a piece of iron on the wall of the shield room in the side near a gantry in which a static magnetic field magnet is built is made. Specifically, a thickness and the like of a piece of iron are adjusted so that isomagnetics of 5 [G] (gauss; 1 [G]=1× $10^{-4}$ [T]) do not leak from a shield room when an MRI apparatus having a super conductive magnet is placed in the shield room. Thereby, it becomes possible to place an MRI apparatus having a super conductive magnet in a shield room for an outdated MRI apparatus having a permanent magnet.

PRIOR TECHNICAL LITERATURE

[Patent literature 1] JPA H05-121227
[Patent literature 2] JPA 2003-135425

However, when a piece of iron is placed on a wall of shield room, the uniformity of a static magnetic field becomes turbulent. The influence on the static magnetic field uniformity by placing a piece of iron is dependent on a distance between the piece of iron and a static magnetic field magnet. That is, the uniformity of a static magnetic field is deteriorated more when a distance between a static magnetic field magnet and an iron is shorter. Therefore, in order to keep the uniformity of a static magnetic field, it is important to secure a required distance between a static magnetic field magnet and a wall of shield room.

On the other hand, in order to secure the space for a bed, the distance from the wall surface of the shield room in the bed side to a static magnetic field magnet becomes longer inevitably compared with the distance from the wall surface of the shield room in the side opposite to the bed. That is, when a high magnetic field type of MRI apparatus having a super conductive magnet is placed in a narrow shield room designed for an outdated MRI apparatus, the portion, in the side opposite to a bed, of the static magnetic field magnet must be close to a wall surface of the shield room.

Therefore, it is desired to develop a technology for keeping the uniformity of a static magnetic field even in a case where a distance between a static magnetic field magnet and a wall surface of a shield room is short. Moreover, not only in a case of replacing an old MRI apparatus with a new one but also in a case where an MRI apparatus is newly placed, it is important to improve the uniformity of a static magnetic field according to a characteristic of shield room and influence by other interfering things.

An object of embodiments of the present invention is to provide a magnetic resonance imaging apparatus, a magnetic field adjustment implement for a magnetic resonance imaging apparatus, a magnetic resonance imaging method, and a method of adjusting a magnetic field for a magnetic resonance imaging apparatus which make it possible to form a static magnetic field having more improved uniformity in an imaging space according to placing circumstance including characteristics of a shield room.

DETAILED DESCRIPTION

In general, according to one embodiment, a magnetic field adjustment implement for a magnetic resonance imaging apparatus includes a magnetic field adjustment unit and a placing unit. The magnetic field adjustment unit is configured to improve a uniformity of a static magnetic field formed by a magnet of the magnetic resonance imaging apparatus. The static magnetic field is formed under an influence of a circumstance in a shield room in which the magnet is placed. The magnetic field adjustment is placed outside the magnet. The placing unit is configured to place the magnetic field adjustment unit outside the magnet.

In addition, a magnetic resonance imaging apparatus according to an embodiment of the present invention includes an imaging unit and a magnetic field adjustment unit. The imaging unit is configured to perform a magnetic resonance imaging by forming a static magnetic field with a magnet and acquiring magnetic resonance signals from an object sent by a bed into an acquisition region of the magnetic resonance signals formed in the magnet. The magnetic field adjustment unit is configured to improve a uniformity of the static magnetic field formed under an influence of a circumstance in a shield room in which the magnet is placed. The magnetic field adjustment is placed outside the magnet.

In addition, a magnetic resonance imaging method according to an embodiment of the present invention includes: performing a magnetic resonance imaging by forming a static magnetic field with a magnet and acquiring magnetic resonance signals from an object sent by a bed into an acquisition region of the magnetic resonance signals formed in the magnet; and arranging a magnetic field adjustment unit outside the magnet and improving a uniformity of the static magnetic field by the magnetic field adjustment unit. The static magnetic field is formed by the magnet. The static magnetic field is formed under an influence of a circumstance in a shield room in which the magnet is placed.

In addition, a method of adjusting a magnetic field for a magnetic resonance imaging apparatus according to an embodiment of the present invention includes: arranging a magnetic field adjustment unit outside a magnet of the magnetic resonance imaging apparatus; and improving a uniformity of a static magnetic field by the magnetic field adjustment unit. The static magnetic field is formed by the magnet. The static magnetic field is formed under an influence of a circumstance in a shield room in which the magnet is placed.

A magnetic resonance imaging apparatus, a magnetic field adjustment implement for a magnetic resonance imaging apparatus, a magnetic resonance imaging method, and a method of adjusting a magnetic field for a magnetic resonance imaging apparatus according to embodiments of the present invention will be described with reference to the accompanying drawings.

First Embodiment

Figure 1:
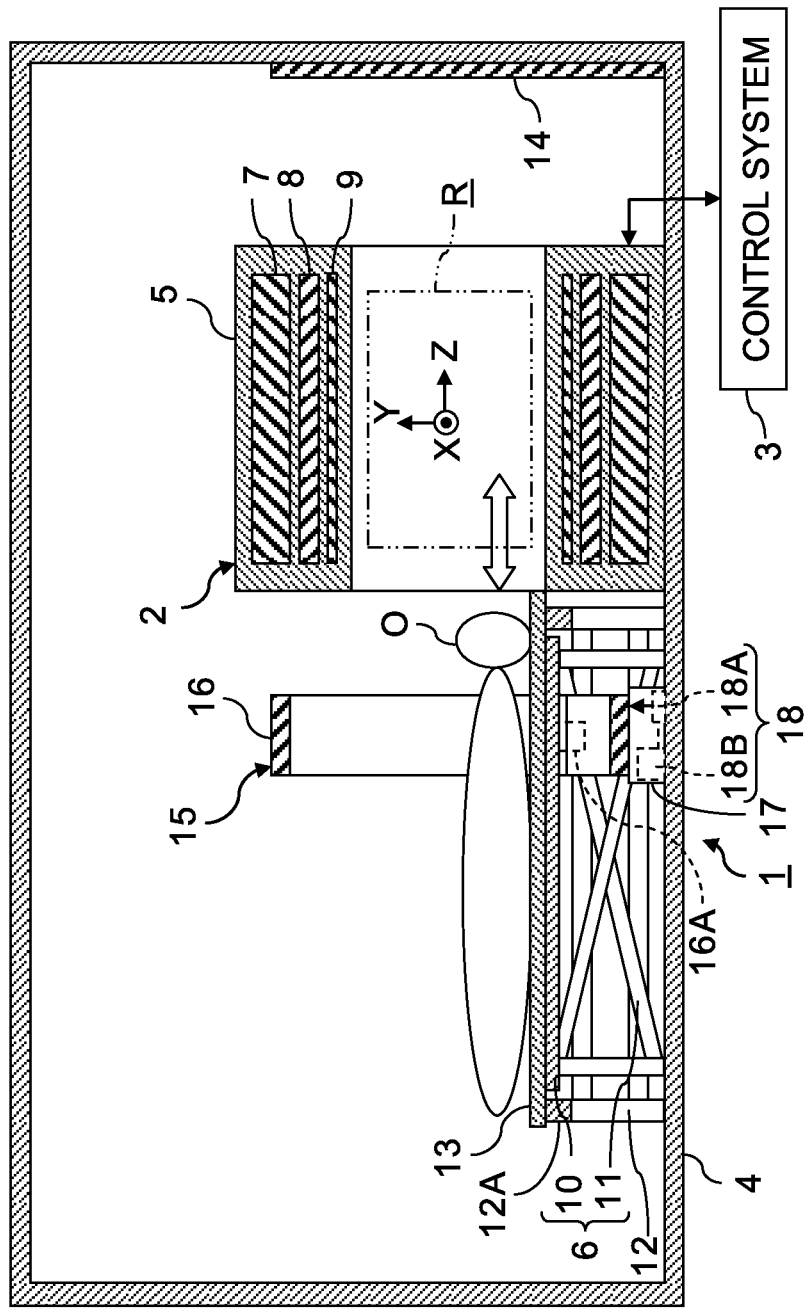
FIG. 1 is a longitudinal sectional view of a magnetic resonance imaging apparatus and a magnetic field adjustment implement for the magnetic resonance imaging apparatus according to the first embodiment of the present invention.

FIG. 1 is a longitudinal sectional view of a magnetic resonance imaging apparatus and a magnetic field adjustment implement for the magnetic resonance imaging apparatus according to the first embodiment of the present invention.

A magnetic resonance imaging apparatus 1 has a data acquisition system 2 and a control system 3. The data acquisition system 2 is placed in a shield room 4 which forms an imaging room. On the other hand, the control system 3 is arranged outside the shield room 4.

The data acquisition system 2 has a function to acquire NMR signals from an object O by applying gradient magnetic field pulses and RF pulses to the object O set under a static magnetic field. For that purpose, the data acquisition system 2 has a gantry 5 and a bed 6. An imaging area is formed in the gantry 5. Further, a cylindrical static magnetic field magnet 7, a cylindrical gradient coil 8, a cylindrical WB (whole body) coil 9 and the like are coaxially built in the gantry 5.

The static magnetic field magnet 7 is a super conductive magnet which has superconductivity coils arranged in cylindrical vacuum vessels and immersed by cooling fluid. The static magnetic field magnet 7 forms the static magnetic field in the imaging area. For an excitation, a static magnetic field the power supply is connected with the superconductivity coils to supply a current. However, the static magnetic field the power supply is generally disconnected with the superconductivity coils after the excitation.

The gradient coil 8 is arranged inside the static magnetic field magnet 7. The gradient coil 8 consists of plural coils which form magnetic fields in the mutually orthogonal X-axis, Y-axis, and Z-axis respectively. The gradient coil 8 has a function to form a gradient magnetic field in the imaging area by controlling a current supplied to each coil constituting the gradient coil 8.

The WB coil 9 is an RF coil arranged inside the gradient coil 8. Although the WB coil 9 is mainly used as an RF coil for transmission which transmits RF pulses to the imaging area, the WB coil 9 is sometimes used for reception of NMR signals.

On the other hand, the bed 6 has a fixed top plate 10 and a bed driving unit 11. On the fixed top plate 10, a movable top plate 13, on which an object O is set, can be placed by a stretcher 12 having two arms 12A. Then, the bed 6 is configured so that the movable top plate 13 on which an object O has been set can be sent into the acquisition region R of NMR signals in the gantry 5 by driving the bed driving unit 11.

In addition, the data acquisition system 2 has local RF coils for transmission of RF signals and reception of NMR signals. Each local RF coil is arranged at an appropriate position in the imaging area formed inside the gantry 5 according to an imaging part or an imaging purpose. For example, a local RF coil, such as an RF coil for head part, which can be detached and attached to the movable top plate 13, a local RF coil directly attached to an object O and the like are known as typical local RF coils.

On the other hand, the control system 3 has a function to output a current or a control signal to each element of the data acquisition system 2 to control the data acquisition system 2, and a function to generate MR image data of an object O based on NMR signals acquired in the data acquisition system 2 by image reconstruction processing and image processing of the NMR signals. For that purpose, the control system 3 has elements including a gradient magnetic field power supply, a transmitter, a receiver, a sequence controller, and a computer. Then, MR imaging of an object O can be performed by control of the data acquisition system 2 by the control system 3 and processing of acquired data.

Moreover, the shield room 4 has a function to reduce the static magnetic field leaking, by the static magnetic field magnet 7, outside the shield room 4, i.e., the shield function to magnetism. Therefore, the shield room 4 generally consists of iron which is easy to be obtained as a ferromagnetic substance. The conditions of the shield room 4, such as a room size and a wall thickness, which influence the shield function, can be appropriately determined so that a leaking magnetic field is sufficiently reduced according to the characteristics of the static magnetic field magnet 7.

However, the magnetic field leaking from the shield room 4 due to the static magnetic field magnet 7 becomes non-negligible when the magnetic resonance imaging apparatus 1 which forms a too high magnetic field has been placed in the shield room 4 designed for placing another magnetic resonance imaging apparatus and when a condition, such as a room size, of the shield room 4 has restriction.

The part where the intensity of the magnetic field leaking outside from the shield room 4 becomes the largest is near the wall surface of the shield room 4 which is closest to the static magnetic field magnet 7. The bed 6 is placed in one side of the gantry 5 in which the static magnetic field magnet 7 is built. Therefore, the part closest to the wall surface of the shield room 4 is the side, opposite to the bed 6, of the gantry 5.

Accordingly, a piece of iron 14 for preventing the leakage of magnetic field is placed on the wall surface of the shield room 4 opposed to the side, opposite to the bed 6, of the gantry 5. For example, conditions including a thickness and a size of the piece of iron 14 are determined so that the 5 [G] of isomagnetics do not leak from the shield room 4.

Furthermore, a magnetic field adjustment implement 15 is provided in the bed 6 side of the gantry 5 in which the static magnetic field magnet 5 is built. The magnetic field adjustment implement 15 has a function to improve the uniformity of the static magnetic field formed, by the static magnetic field magnet 7, under the influence of the circumstance in the shield room 4 in which the static magnetic field magnet 7 is placed.

Namely, the static magnetic field formed by the static magnetic field magnet 7 is subject to the influence of magnetic bodies, such as a metal, placed in the shield room 4. For example, the piece of iron 14 which leads the magnetic flux lines to the inside is placed in the side, opposite to the bed 6, of the static magnetic field magnet 7. However, no piece of iron 14 can be placed at the symmetrical position in the bed 6 side of the static magnetic field magnet 7. As a result, the non-uniformity arises in the static magnetic field due to the influence of the piece of iron 14. In addition, other objects, such as the bed 6 and the stretcher 12, containing metal and placed in the shield room 4 also influences the static magnetic field.

Accordingly, the magnetic field adjustment implement 15 is configured to improve the uniformity of the static magnetic field according to the circumstance in the shield room 4. For that purpose, the magnetic field adjustment implement 15 has a cancel coil 16, a placing member 17, and a control unit 18.

Figure 2:
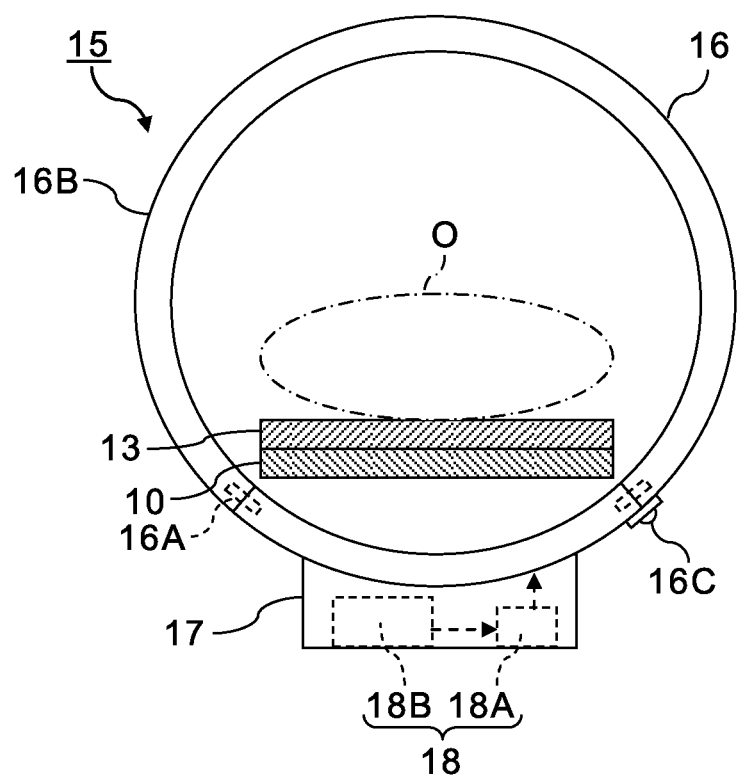
FIG. 2 is a left side view of the cancel coil shown in FIG. 1.

FIG. 2 is a left side view of the cancel coil 16 shown in FIG. 1.

The cancel coil 16 has a function to improve the uniformity of the static magnetic field in the acquisition region R of NMR signals by canceling the influence, due to other elements, on the static magnetic field formed by the static magnetic field magnet 7. Especially, the cancel coil 16 is configured to cancel the influence, on the static magnetic field, by at least the piece of iron 14 placed on the wall surface of the shield room 4.

The placing member 17 is a part for placing the cancel coil 16 at a suitable position in the bed 6 side of the gantry 5. For example, when the cancel coil 16 is placed on the floor of the shield room 4, the placing member can be made by an object which has a predetermined weight. Alternatively, when the cancel coil 16 is fixed to the shield room 4 or an element of the magnetic resonance imaging apparatus 1, the placing member 17 can be made by fixing material, such as welding metal, or attachment implements, such as a bolt and nut or a socket.

The cancel coil 16 is a coil which mainly cancels the influence, on the static magnetic field, by the piece of iron 14. Therefore, the cancel coil 16 should be placed at least in the bed 6 side, outside the acquisition region R of NMR signals, in the shield room 4. For example, by arranging the cancel coil 16 in the bed 6 side of the gantry 5 by the placing member 17, the cancel coil 16 can be placed easily even after placing the gantry 5. FIG. 1 and FIG. 2 show an example of arranging the cancel coil 16 by the placing member 17 so that the fixed top plate 10 of the bed 6 lies inside the cancel coil 16.

Note that, when the distance between the cancel coil 16 and the static magnetic field magnet 7 in the gantry 5 is made short, the magnetic field component which degrades the uniformity of the static magnetic field can be fully canceled even if the ampere-turn (NI [A]), represented by a product of the number N of the coil winding of the cancel coil 16 with a current I [A], is set to be small. That is, power consumption can be made smaller when the cancel coil 16 is arranged closer to the static magnetic field magnet 7.

Alternatively, if a current is constant, the diameter and the number of turns of the cancel coil 16 can be made small. Consequently, the adverse effect to the operativity due to placing the cancel coil 16 can be reduced.

Accordingly, FIG. 1 and FIG. 2 show an example of arranging the cancel coil 16 at a position away from the gantry 5 and shifted a little from the end part of the bed 6 toward the center, by the placing member 17, so that a work space can be obtained near the gantry 5 side of the bed 6.

Moreover, in order to suppress the adverse effect to the operativity due to the installation of the cancel coil 16 further, the cancel coil 16 can be configured to be divisible using connectors 16A. For example, two coil parts 16B composing the divided upper part and lower part of the cancel coil 16 can be connected by the two connectors 16A so that the two coil parts 16B can be detached mutually as shown in FIG. 2. Furthermore, if one end of one coil part 16B is connected with that of the other coil part 16B by a hinge 16C, the cancel coil 16 can be opened and closed.

Figure 3:
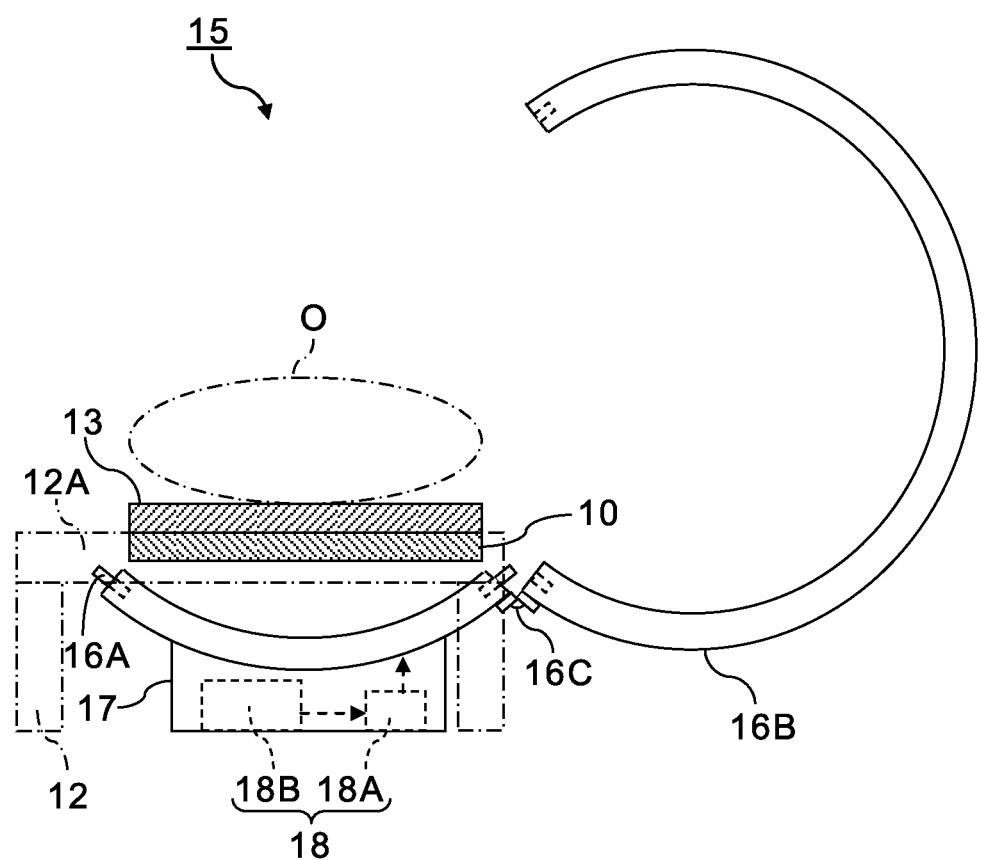
FIG. 3 is a view showing the state where the cancel coil shown in FIG. 2 was divided.

FIG. 3 is a view showing the state where the cancel coil 16 shown in FIG. 2 was divided.

When the coil parts 16B of the cancel coil 16 is connected mutually using the hinge 16C and the connectors 16A as shown in FIG. 3, the cancel coil 16 can be opened and closed. Thereby, the interference by the cancel coil 16 can be avoided in installation of the movable top plate 13 using the stretcher 12 or setting an object O. That is, it becomes possible to set an object O and the movable top plate 13 using the stretcher 12 easily.

On the other hand, the control unit 18 is a device which controls the current supplied to the cancel coil 16. The control unit 18 can be composed using a power supply 18A and a computer 18B. As shown in FIG. 1, FIG. 2, and FIG. 3, the control unit 18 can be put inside the placing member 17.

The power supply 18A is configured to supply a current to the cancel coil 16 according to the control signal from the computer 18B.

By installing a program into the operation unit of the computer 18B, the control function of the power supply 18A can be provided with the computer 18B. Therefore, the optimal current according to the circumstance in the shield room 4 can be supplied to the cancel coil 16 from the power supply 18A, for improving the uniformity of the static magnetic field in the acquisition region R of NMR signals, by control of the power supply 18A by the computer 18B.

The suitable current value which should be supplied to the cancel coil 16 can be preliminarily measured as the current value when the uniformity of the static magnetic field becomes the best, by adjusting a supplied current to the cancel coil 16 in the time of installation of the magnetic resonance imaging apparatus 1 or at a periodical maintenance. Alternatively, the suitable current value for the cancel coil 16 according to the circumstance in the shield room 4 may be calculated by a simulation.

The current value which should be supplied to the cancel coil 16 varies according to objects, which influence the static magnetic field, placed in the shield room 4. That is, in addition to the piece of iron 14 placed in the shield room 4, the current value which should be supplied to the cancel coil 16 also varies according to conditions including a type of the bed 6 and whether the stretcher 12 is used or not.

Accordingly, the suitable current values which should be supplied to the cancel coil 16, according to circumstances such as objects placed in the shield room 4, obtained by measurement or calculation can be stored as preset values in the storage unit of the computer 18B. That is, the suitable current values to the cancel coil 16 for respective kinds of objects placed in the shield room 4 can be stored as a table of preset values in the storage unit.

Then, a current having a current value corresponding to a circumstance in the shield room 4 can be supplied from the power supply 18A to the cancel coil 16 by reading the current value corresponding to the circumstance in the shield room 4 from storage unit of the computer 18B and outputting the current value as a control signal from the computer 18B to the power supply 18A. Thereby, the influence of placed objects on the uniformity of the static magnetic field can be canceled by the magnetic field formed by the cancel coil 16 even in a case where a more detailed magnetic field circumstance has been changed, like a case of replacing the bed 6 in the shield room 4 or a case of using the stretcher 12.

When the magnetic field adjustment implement 15 is placed in the shield room 4, the reduction effect of the magnetic field leaking from the shield room 4 can also be acquired in addition to the above-mentioned effect of improvement in the uniformity of the static magnetic field in the acquisition region R of NMR signals. Therefore, the desired number of the magnetic field adjustment implements 15 may be arranged at desired positions outside the static magnetic field magnet 7.

For example, if the magnetic field adjustment implement 15 including the cancel coil 16 is placed in the side, opposite to the bed 6, of the static magnetic field magnet 7, the magnetic field leaking from the shield room 4 and facing the side, opposite to the bed 6, of the static magnetic field magnet 7 can be reduced. Therefore, if the cancel coil 16 is placed in the side, opposite to the bed 6, of the gantry 5, the magnetic field leaking from the shield room 4 can be suppressed in adapting to the magnetic field circumstance in the shield room 4 more satisfactorily than the piece of iron 14. Consequently, the piece of iron 14 can be omitted.

On the contrary, if the cancel coil 16 is arranged near an object O in the bed 6 side of the gantry 5, an effect that a metal can be detected by detecting an unusual current change in the cancel coil 16 can be also obtained when the metal is attached to the object O. Thereby, an attracting accident that a metal attached to an object O is attracted by the static magnetic field magnet 7 can be also prevented.

The cancel coil 16 may be fixed or standed on a desired subject so long as the cancel coil 16 is in the shield room 4. FIG. 1, FIG. 2, and FIG. 3 show an example of standing the cancel coil 16 on the floor of the shield room 4 by the placing member 17. However, the cancel coil 16 may be fixed on a target, such as the bed 6 or the gantry 5, by the placing member 17. Moreover, the cancel coil 16 may be also arranged inside the gantry 5.

Figure 4:
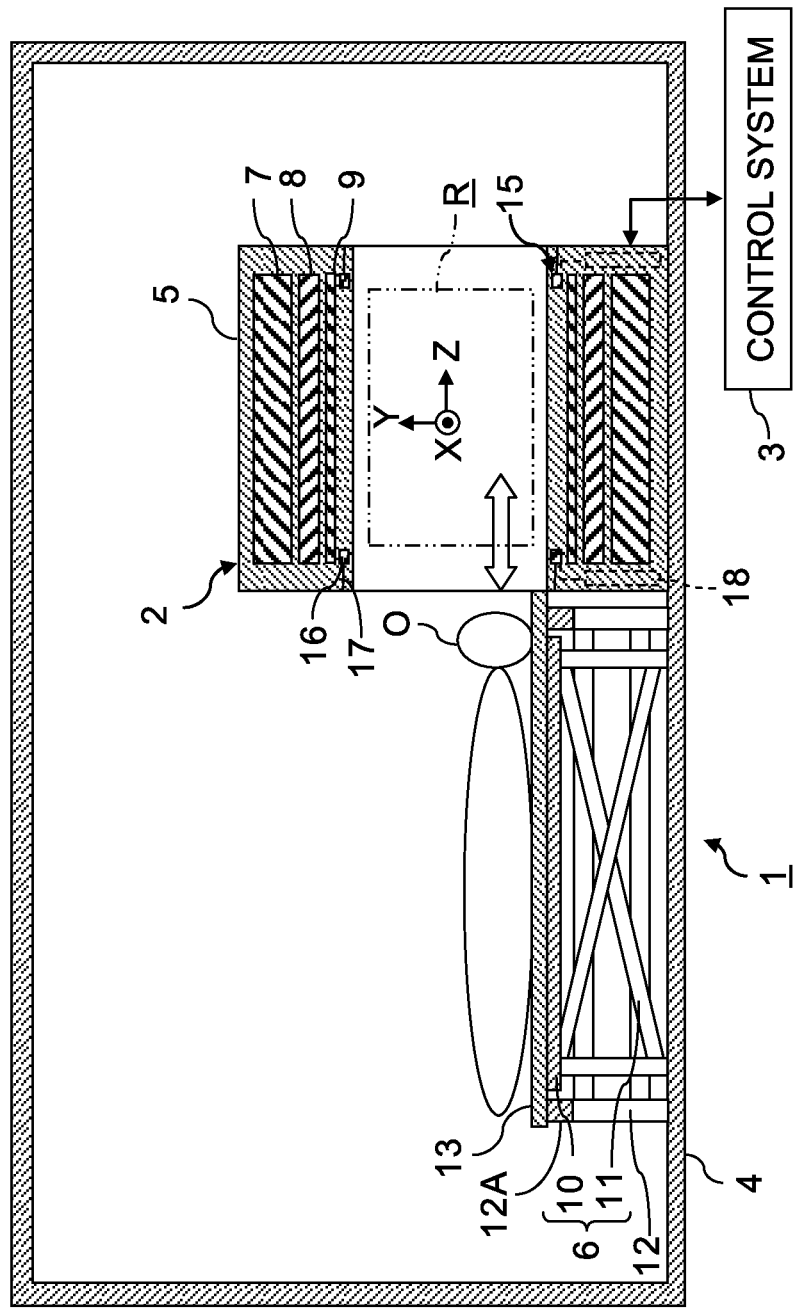
FIG. 4 is a view showing an example of arranging the magnetic field adjustment implement including the cancel coil in the gantry shown in FIG. 1.

FIG. 4 is a view showing an example of arranging the magnetic field adjustment implement 15 including the cancel coil 16 in the gantry 5 shown in FIG. 1.

For example, the cancel coil 16 of the magnetic field adjustment implement 15 can be built in each side, outside the acquisition region R of NMR signals, in the gantry 5 as shown in FIG. 4. That is, the cancel coils 16 can be fixed inside the gantry 5 by the placing members 17 respectively.

In this case, if the cancel coil 16 is arranged in the internal side or the external side of the static magnetic field magnet 7, the length of the gantry 5 in the axial direction can be shortened. FIG. 4 shows an example of arranging the cancel coils 16 in the internal side the WB coil 9. However, the cancel coils 16 may be arranged in gaps between elements in the gantry 5 or outside the both ends of the static magnetic field magnet 7 in the gantry 5.

If the cancel coils 16 are built in the gantry 5 as shown in FIG. 4, the space in the shield room 4 can be used effectively. Moreover, the cancel coils 16 can be close to the static magnetic field magnet 7. Furthermore, the control unit 18 of the cancel coils 16 can be also built in the gantry 5 or arranged outside the gantry 5. Note that, if the cancel coil 16 is also arranged in the side, opposite to the bed 6, of the static magnetic field magnet 7 as shown in FIG. 4, the piece of iron 14 placed to the wall surface of the shield room 4 can be omitted.

According to the magnetic resonance imaging apparatus 1 and the magnetic field adjustment implement 15 configured as described above, the prevention of the magnetic field leaking from the shield room 4 to the outside and the improvement in the uniformity of the static magnetic field can be achieved by the piece of iron 14 and the magnetic field adjustment implement 15 placed in the both sides of the static magnetic field magnet 7 even if the static magnetic field magnet 7 is placed closer to the wall surface of the shield room 4 than before. In other words, the magnetic resonance imaging apparatus 1 can be placed even in the shield room 4 which may be narrow compared with a conventional one.

As a result, it becomes possible to introduce the magnetic resonance imaging apparatus 1 having a super conductive magnet, which forms a high magnetic field of 1.5 [T] and above, in a shield room designed for a low magnetic field type of a magnetic resonance imaging apparatus having a normal conduction magnet or a permanent magnet.

For example, even in a case where the piece of iron 14 for prevention of the leaking magnetic field is placed on the wall surface of the shield room 4 nearest to the gantry 5 as shown in FIG. 1, the uniformity of the static magnetic field can be kept appropriately.

Figure 5:
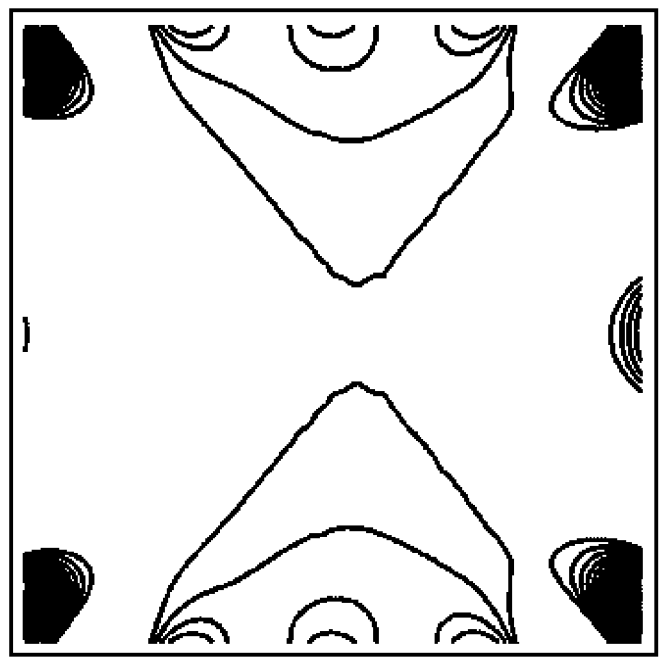
FIG. 5 shows graphs for comparing a simulation result of a static magnetic field formed by the static magnetic field magnet in the case where the magnetic field adjustment implement is arranged in the shield room, to which the piece of iron is placed, shown in FIG. 1, with that in the case where the magnetic field adjustment implement is not arranged.
Figure 5:
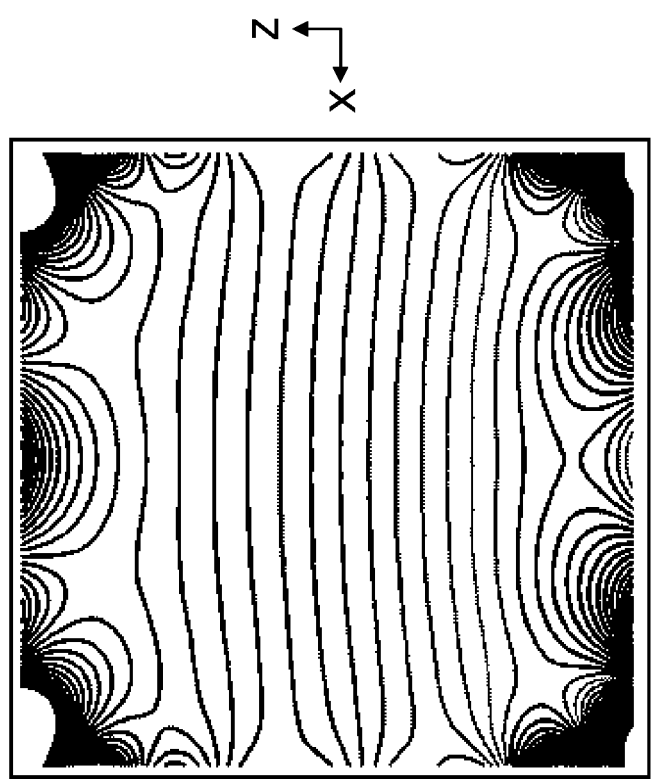

FIG. 5 shows graphs for comparing a simulation result of a static magnetic field formed by the static magnetic field magnet 7 in the case where the magnetic field adjustment implement 15 is arranged in the shield room 4, to which the piece of iron 14 is placed, shown in FIG. 1, with that in the case where the magnetic field adjustment implement 15 is not arranged.

In (A) and (B) of FIG. 5, each horizontal axis denotes the X-axis of an imaging area, each vertical axis denotes the Z-axis of the imaging area, each curve denotes an isomagnetic line on the 0.5 [m]×0.5 [m] of XZ plane. Moreover, FIG. 5 (A) shows a simulation result of a static magnetic field distribution formed on the XZ plane without the magnetic field adjustment implement 15. Meanwhile, FIG. 5 (B) shows a simulation result of a static magnetic field distribution formed on the XZ plane with the magnetic field adjustment implement 15.

If the piece of iron 14 is placed on the wall surface of the shield room 4 as shown in FIG. 1, the static magnetic field formed by the 1.5 [T] of static magnetic field magnet 7 shows a distribution as shown in FIG. 5 (A) under the influence of the piece of iron 14. In this case, it is experientially known that the gradient of the static magnetic field in the Z-axis direction becomes almost linear. That is, the one order of linear component referred to as the Z1 term is dominant to the distortion of the static magnetic field in the Z-axis direction. Therefore, the interval between isomagnetic lines in the Z-axis direction is even approximately.

On the other hand, if the cancel coil 16 whose NI=6 [kA] and radius R=500 mm is placed at the position away from the center of the static magnetic field by 1200 mm, i.e., at the position where Z=−1200 mm, a static magnetic field distribution as shown in FIG. 5 (B) is formed. According to FIG. 5 (B), it can be recognized that the interval between isomagnetic lines is remarkably larger than that shown in FIG. 5 (A). That is, the density of isomagnetic lines has decreased remarkably. This shows that the uniformity of the static magnetic field has been improved by installation of the magnetic field adjustment implement 15. Especially, it can be recognized that the uniform static magnetic field has been formed in the Z-axis direction.

Therefore, according to the magnetic resonance imaging apparatus 1 for which the magnetic field adjustment implement 15 has been placed, MR images having an improved image quality can be acquired by MR imaging under the static magnetic field having high uniformity.

Second Embodiment

Figure 6:
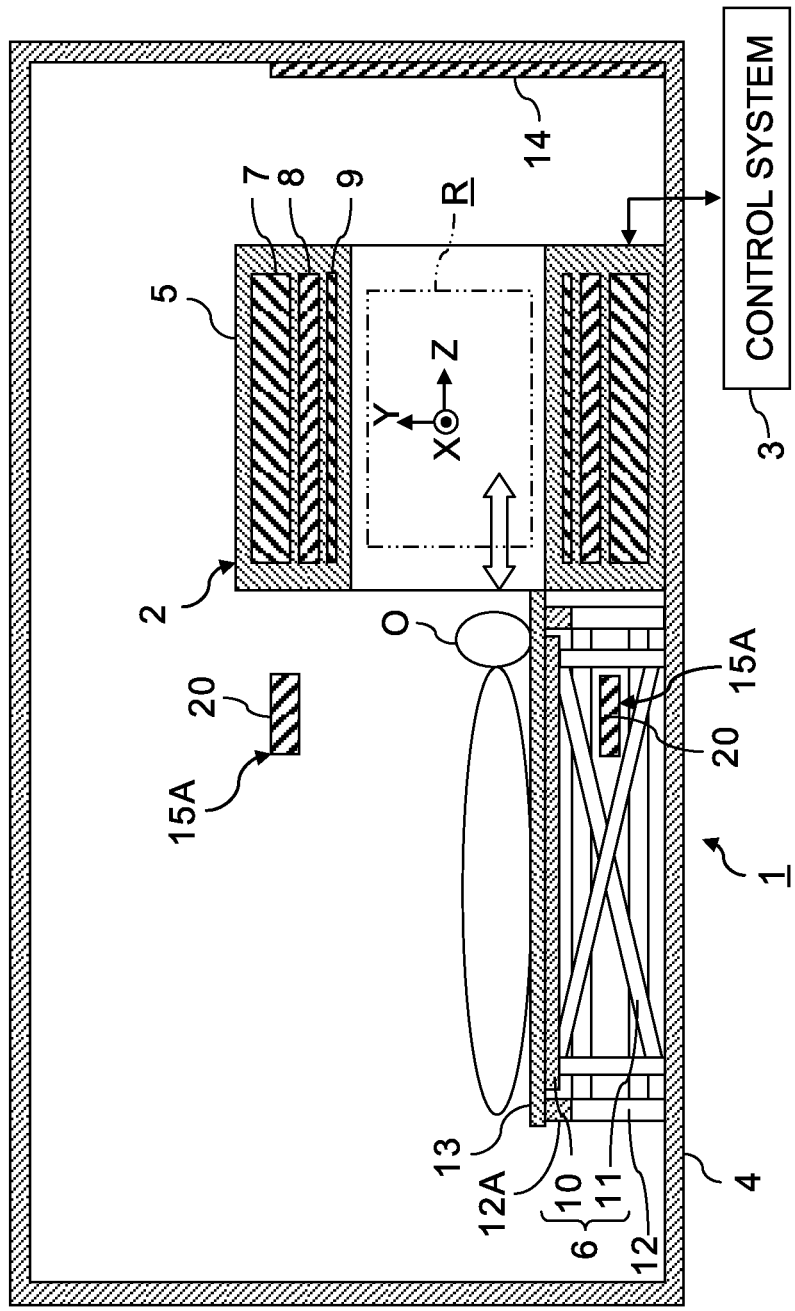
FIG. 6 is a longitudinal sectional view of a magnetic resonance imaging apparatus and a magnetic field adjustment implement for the magnetic resonance imaging apparatus according to the second embodiment of the present invention.
Figure 7:
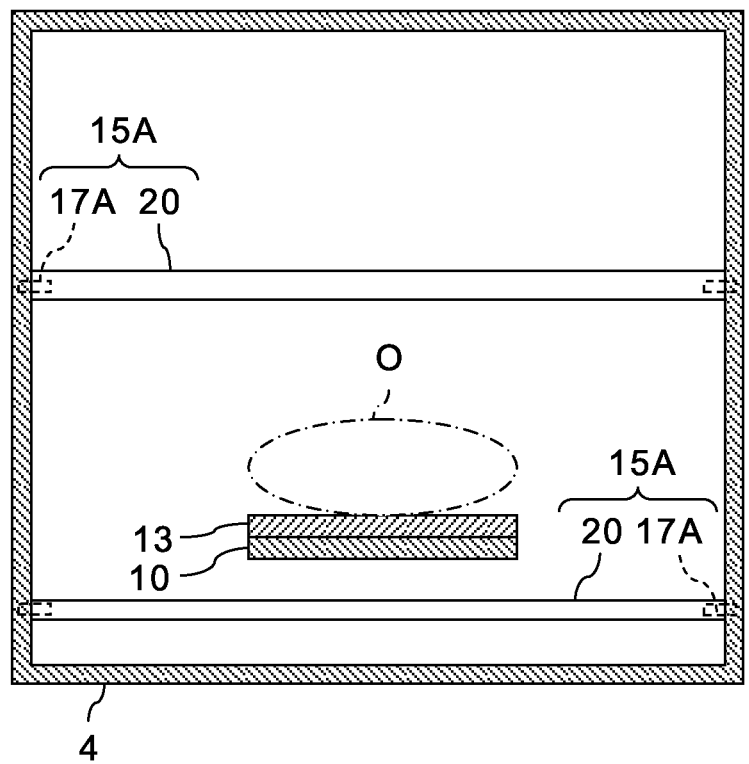
FIG. 7 is a left side view of the magnetic field adjustment implement shown in FIG. 6.

FIG. 6 is a longitudinal sectional view of a magnetic resonance imaging apparatus and a magnetic field adjustment implement for the magnetic resonance imaging apparatus according to the second embodiment of the present invention. FIG. 7 is a left side view of the magnetic field adjustment implement shown in FIG. 6.

A magnetic resonance imaging apparatus 1 and a magnetic field adjustment implement 15A in the second embodiment shown in FIG. 6 and FIG. 7 differ from the magnetic resonance imaging apparatus 1 and the magnetic field adjustment implement 15 in the first embodiment only in a composition of the magnetic field adjustment implement 15A. Therefore, only the composition of the magnetic field adjustment implement 15A is explained. Note that, the same signs are attached to the other elements and explanation thereof is omitted.

The magnetic field adjustment implement 15A in the second embodiment is configured by fixing a ferromagnetic substance, having a desired shape, for improving the uniformity of the static magnetic field, at a desired position by the placing member 17A. As the ferromagnetic substance, iron, cobalt, and iron-cobalt alloy are typical. However, using iron as the ferromagnetic substance is practical because the iron is inexpensive and easy to be obtained. Accordingly, an example case where the ferromagnetic substance is iron will be described hereafter.

The magnetic field adjustment implement 15A shown in FIG. 6 and FIG. 7 can be composed with iron poles 20, as an example of the ferromagnetic substance, and placing members 17A. Each iron pole 20 is placed at least in the bed 6 side and outside the acquisition region R of NMR signals formed inside the static magnetic field magnet 7, by the placing members 17A. In the example shown in FIG. 6 and FIG. 7, the two iron poles 20 whose longitudinal directions are the horizontal direction perpendicular to the sending direction of the bed 6 have been fixed in the upper and lower sides of the bed 6, between the wall surfaces of the shield room 4, by the placing members 17A such as bolts or clasps.

As a result, a magnetic circuit which leads the magnetic flux lines generated by the static magnetic field magnet 7 is formed by the shield room 4 and the iron poles 20. That is, the magnetic flux lines in the bed 6 side generated by the static magnetic field magnet 7 are attracted toward the iron poles 20. Then, the attracted magnetic flux lines are led in the wall surfaces of the shield room 4 through the interior portions of the iron poles 20. Furthermore, the magnetic flux lines reach the side, opposite to the bed 6, of the static magnetic field magnet 7 through the interior portions of the wall surfaces of the shield room 4.

Therefore, the uniformity of the static magnetic field in the acquisition region R of NMR signals can be improved by arranging the iron poles 20, each having a suitable shape, at suitable positions by the placing members 17A. That is, the influence, by the piece of iron 14 and the like, on the static magnetic field in the acquisition region R of NMR signals can be canceled by formation of the ideal magnetic circuit by installation of the iron poles 20.

Note that, the size of each iron pole 20 can be made small when the distance between the iron pole 20 and the static magnetic field magnet 7 is made short. Therefore, if the iron poles 20 are arranged close to the static magnetic field magnet 7, the work space in the shield room 4 can be secure by making the thicknesses of the iron poles 20 thin. However, the iron poles 20 may be fixed to positions away from the gantry 5 and shifted a little from the end part of the bed 6 toward the center, by the placing members 17A, so that a work space can be obtained near the gantry 5 side of the bed 6, as shown in FIG. 6.

On the contrary, as long as the uniformity of the static magnetic field in the acquisition region R of NMR signals can be improved, the iron poles 20 may be fixed to interior portions of the gantry 5 by the placing members 17A.

Moreover, the iron poles 20 may be fixed between the ceiling and the floor of the shield room 4. Furthermore, not only the iron pole 20 but an iron member, such as an iron ring, having an arbitrary shape may be fixed in the shield room 4 by the placing members 17A.

Figure 8:
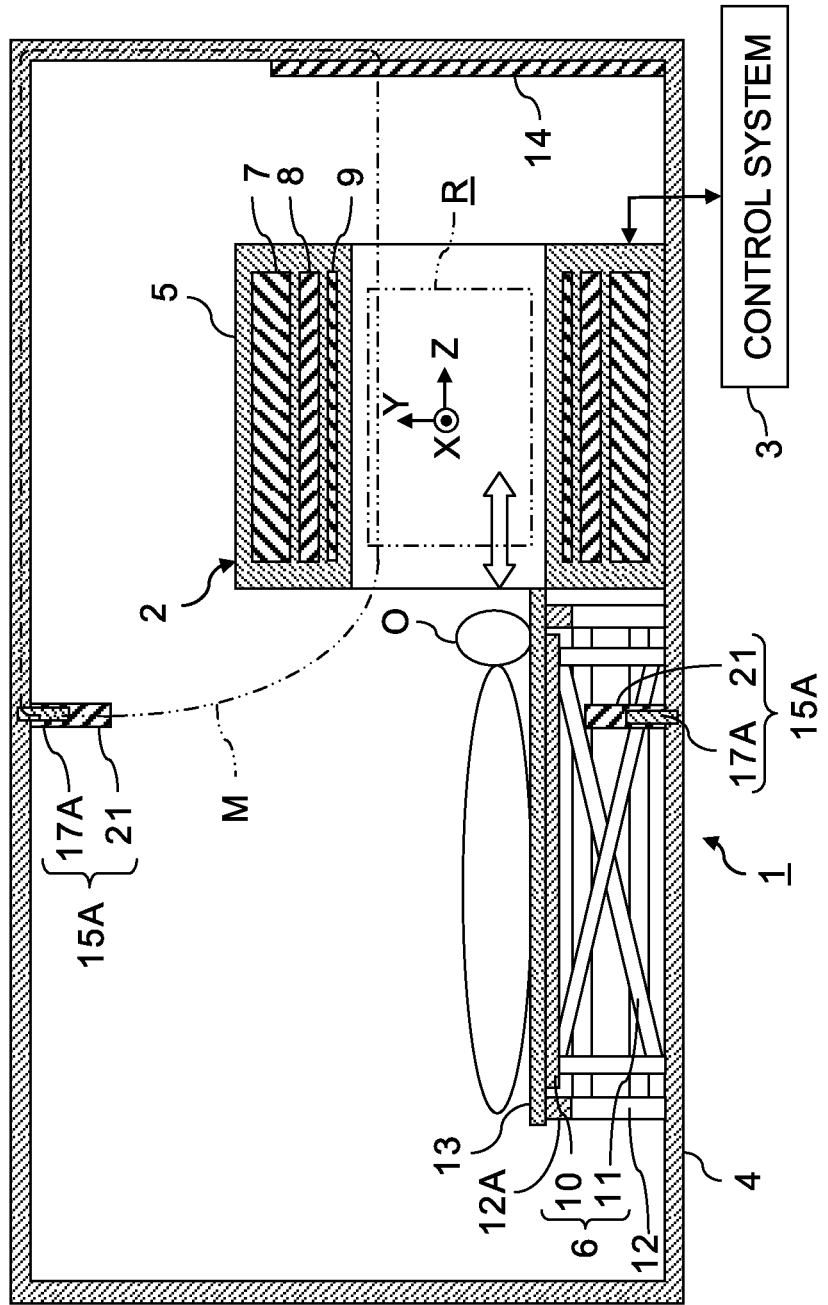
FIG. 8 is a view showing an example of fixing iron ribs to the shield room as the magnetic field adjustment implement shown in FIG. 6.
Figure 9:
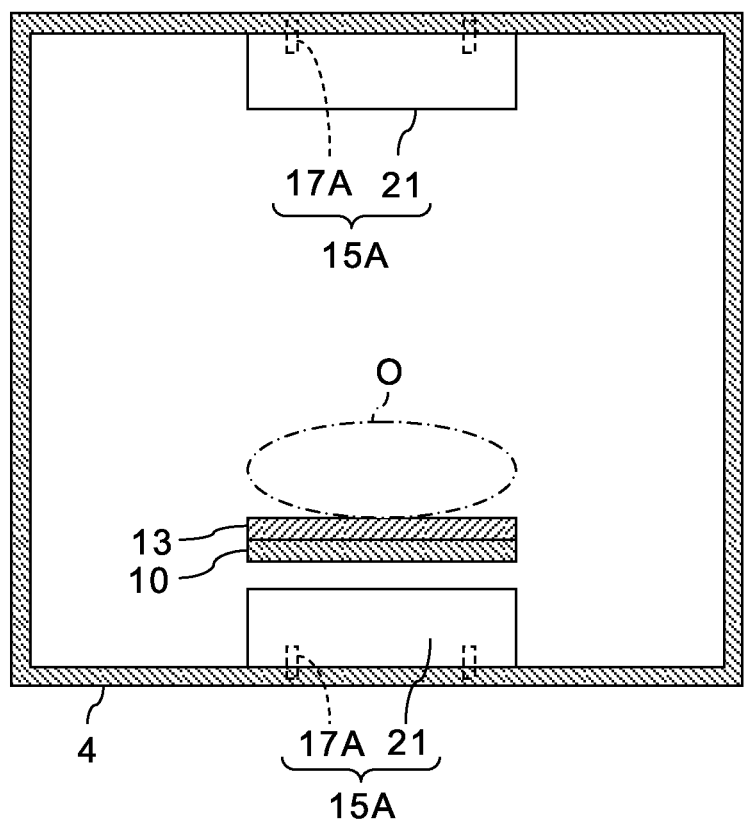
FIG. 9 is a left side view of the magnetic field adjustment implement shown in FIG. 8.

FIG. 8 is a view showing an example of fixing iron ribs to the shield room 4 as the magnetic field adjustment implement 15A shown in FIG. 6. FIG. 9 is a left side view of the magnetic field adjustment implement 15A shown in FIG. 8.

As shown in FIG. 8 and FIG. 9, iron ribs 21 may be attached to arbitrary parts, e.g., the ceiling and the floor, of the shield room 4 by placing members 17A to compose the magnetic field adjustment implement 15A. The sizes including heights, thicknesses, and widths of the iron ribs 21 can be made small when the distances between the iron ribs 21 and the static magnetic field magnet 7 are small. Therefore, if each iron rib 21 is arranged at a position near the static magnetic field magnet 7, the space in the shield room 4 can be used effectively.

When the iron ribs 21 nearly perpendicular to the wall surfaces of the shield room 4 are arranged, a magnetic circuit which leads the magnetic flux lines M generated by the static magnetic field magnet 7 is formed by the iron ribs 21 and the shield room 4 as shown in FIG. 8 and FIG. 9. Specifically, the magnetic flux lines M, in the bed 6 side, generated by the static magnetic field magnet 7 are attracted toward the iron ribs 21 in the bed 6 side and outside the acquisition region R of NMR signals formed in the static magnetic field magnet 7. Then, the attracted magnetic flux lines M are led in the wall surfaces of the shield room 4 through the interior portions of the iron ribs 21. Furthermore, the magnetic flux lines M reach the side, opposite to the bed 6, of the static magnetic field magnet 7 through the interior portions of the wall surfaces of the shield room 4.

Note that, even if a gap exists between the iron rib 21 and the shield room 4, a magnetic circuit similar to that in the case where the iron rib 21 is contacted to the shield room 4 can be formed so long as the gap is narrow enough.

Therefore, the uniformity of the static magnetic field in the acquisition region R of NMR signals can be improved by fixing the iron ribs 21, each having a suitable shape, to suitable positions in the shield room 4 by the placing members 17A. That is, the influence, by the piece of iron 14 and the like, on the static magnetic field in the acquisition region R of NMR signals can be canceled by formation of the ideal magnetic circuit by installation of the iron ribs 21.

That is, the magnetic field adjustment implement 15A in the second embodiment is configured by using a ferromagnetic substance, such as iron, instead of the cancel coil 16 included in the magnetic field adjustment implement 15 in the first embodiment. Therefore, according to the second embodiment, the magnetic field adjustment implement 15A can be easily placed in the shield room 4 at a low cost. Moreover, the magnetic field adjustment implement 15A can be firmly fixed in the shield room 4. The magnetic field adjustment implement 15A is effective especially when influence, constantly arising with a small change, on the static magnetic field should be reduced

Third Embodiment

Figure 10:
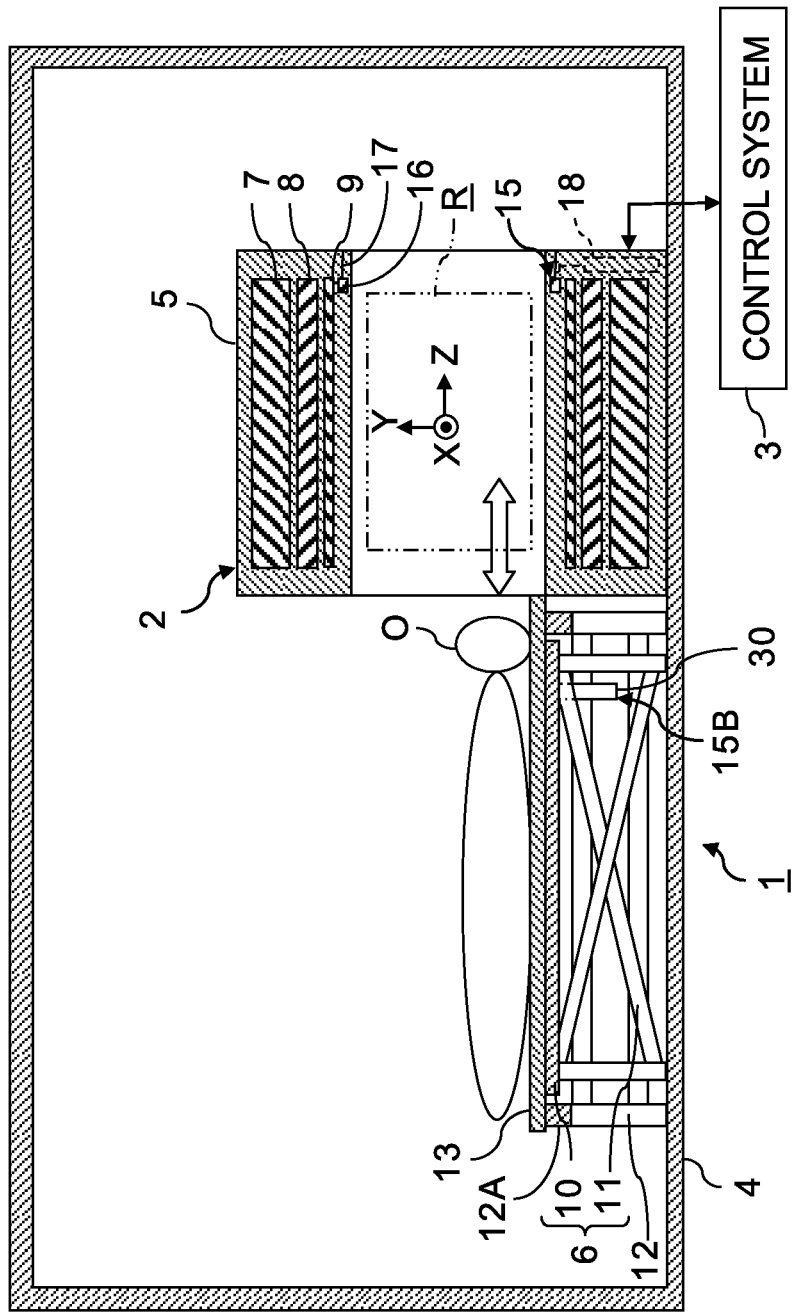
FIG. 10 is a longitudinal sectional view of a magnetic resonance imaging apparatus and a magnetic field adjustment implement for the magnetic resonance imaging apparatus according to the third embodiment of the present invention.

FIG. 10 is a longitudinal sectional view of a magnetic resonance imaging apparatus and a magnetic field adjustment implement for the magnetic resonance imaging apparatus according to the third embodiment of the present invention.

A magnetic resonance imaging apparatus 1 in the third embodiment shown in FIG. 10 differs from each magnetic resonance imaging apparatus 1 of the first and second embodiments only in a composition of the magnetic field adjustment implement. Therefore, only the composition of the magnetic field adjustment implement is explained. Note that, the same signs are attached to the other elements and explanation thereof is omitted.

In the magnetic resonance imaging apparatus 1 in the third embodiment, a cancel coil 16 for improving the uniformity of the static magnetic field as shown in FIG. 4 is placed as the first the magnetic field adjustment implement 15 in the side, opposite to the bed 6, outside the acquisition region R of NMR signals formed in the static magnetic field magnet 7. In an example shown in FIG. 10, the cancel coil 16 has been fixed to the inside of the gantry 5, in which the static magnetic field magnet 7 is built, by placing members 17. Moreover, the current supplied to the cancel coil 16 can be controlled by a control unit 18.

Furthermore, in the magnetic resonance imaging apparatus 1, a ferromagnetic substance 30 having an arbitrary shape is placed to the bed 6, as the second the magnetic field adjustment implement 15B. Note that, an example of arranging the platy ferromagnetic substance 30 in the lower part of the fixed top plate 10 of the bed 6 as a part added to the bed 6 is shown in FIG. 10. However, an element of the bed 6 may be made by the ferromagnetic substance 30. Moreover, the ferromagnetic substance 30 may not be directly arranged to the bed 6 so long as the ferromagnetic substance 30 is arranged at least in the bed 6 side. That is, the ferromagnetic substance 30 can be arranged in the bed 6 or the bed 6 side as a part of bed 6 or a part added to the bed 6.

Moreover, it is preferable to arrange the ferromagnetic substance 30 close to the static magnetic field magnet 7 as mentioned above. Therefore, in order to satisfy this requirement, it may be desired to arrange the ferromagnetic substance 30 at a position moved with the top plate which moves in the up-and-down direction. In such a case, it is important to arrange the ferromagnetic substance 30 so that its height changes together with the top plate of the bed 6 and the uniformity of the static magnetic field is improved by the ferromagnetic substance 30 when the height of the top plate has become the height for sending the top plate into the acquisition region R of NMR signals.

In addition, it is important to configure the bed 6 so that the top plate can be moved with a larger torque than the magnetic force attracting the ferromagnetic substance 30 to the static magnetic field magnet 7.

According to the magnetic resonance imaging apparatus 1 in the third embodiment as described above, an effect equivalent to that in the magnetic resonance imaging apparatus 1 shown in FIG. 4 can be obtained. That is, the magnetic field leaking from the shield room 4 can be prevented by the cancel coil 16 arranged in the side opposite to the bed 6. As a result, the piece of iron 14 placed on the wall surface of the shield room 4 can be omitted.

On the other hand, the magnetic flux lines in the bed 6 side generated by the static magnetic field magnet 7 are attracted toward the ferromagnetic substance 30 arranged in the bed 6 side. Then, the influence of the cancel coil 16 on the static magnetic field in the acquisition region R of NMR signals can be canceled by formation of a magnetic circuit. As a result, the magnetic field uniformity in the acquisition region R of NMR signals can be improved.

OTHER EMBODIMENTS

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, the above-mentioned first embodiment may be combined with the second embodiment like the third embodiment. That is, both the cancel coil 16 and the ferromagnetic substance such as iron can be arranged as the magnetic field adjustment implements 15, 15A in the shield room 4 in which the static magnetic field magnet 7 of the magnetic resonance imaging apparatus 1 is placed.

Namely, the magnetic field adjustment implements 15, 15A, 15B, which improves the uniformity of the static magnetic field formed by the static magnetic field magnet 7 under the influence of the circumstance in the shield room 4 in which the static magnetic field magnet 7 is placed, can be arranged at various positions outside the static magnetic field magnet 7 of the magnetic resonance imaging apparatus 1 by the placing members 17, 17A or the like. Then, MR imaging can be performed by forming the static magnetic field by the static magnetic field magnet 7 and acquiring NMR signals from an object O sent, by the bed 6, into the acquisition region R of NMR signals formed in the static magnetic field magnet 7.

What is claimed is:

1. A magnetic field adjustment implement for a magnetic resonance imaging (MRI) apparatus comprising:
   a magnetic field adjustment structure placed and configured to improve uniformity of a static magnetic field formed in an MRI signal acquisition region within and surrounded by a cylindrical static MRI magnet in a magnetically shielded room, the magnetic field adjustment structure being placed outside the cylindrical static MRI magnet,
   wherein a bed of the magnetic resonance apparatus is located on a first side of the acquisition region and at least a part of the bed is arranged to be moved into the acquisition region towards an opposite second side of the acquisition region, and
   wherein said magnetic field adjustment structure is placed outside the acquisition region on at least one of said sides.

2. The magnetic field adjustment implement for the magnetic resonance imaging apparatus of claim 1,
   wherein said magnetic field adjustment structure includes a coil configured to improve uniformity of the static magnetic field.

3. The magnetic field adjustment implement for the magnetic resonance imaging apparatus of claim 2,
   wherein said coil is placed at the second side outside the acquisition region.

4. The magnetic field adjustment implement for the magnetic resonance imaging apparatus of claim 1,
   wherein said magnetic field adjustment structure includes a ferromagnetic substance configured to improve uniformity of the static magnetic field.

5. The magnetic field adjustment implement for the magnetic resonance imaging apparatus of claim 4,
   wherein said ferromagnetic substance is placed as a part of, or as a part added to, the bed.

6. The magnetic field adjustment implement for the magnetic resonance imaging apparatus of claim 1,
   wherein said magnetic field adjustment structure comprises:
   a coil configured to improve uniformity of the static magnetic field;
   a data storage configured to store current values to be supplied to said coil according to placed objects in the shield room, the objects each influencing the static magnetic field; and
   a current supply configured to supply a current to said coil, the current having a current value read from said storage.

7. The magnetic field adjustment implement for the magnetic resonance imaging apparatus of claim 1,
   wherein said magnetic field adjustment structure includes a coil which is configured to be divided with a connector, the coil improving uniformity of the static magnetic field, and
   said coil is placed so as to set a top plate of the bed inside said coil.

8. The magnetic field adjustment implement for the magnetic resonance imaging apparatus of claim 1,
   wherein said magnetic field adjustment structure has a coil configured to improve uniformity of the static magnetic field; and
   said coil is placed inside a gantry in which the magnet is built.

9. The magnetic field adjustment implement for the magnetic resonance imaging apparatus of claim 1,
   wherein said magnetic field adjustment structure includes a ferromagnetic substance configured to form a magnetic circuit with the shield room by leading magnetic flux lines to the shield room, the magnetic flux lines being formed by the magnet and passing inside said ferromagnetic substance, the magnetic circuit being formed at the first side outside the acquisition region.

10. A magnetic resonance imaging (MRI) apparatus comprising:
    an imager configured to perform MRI by forming a static magnetic field with a cylindrical static MRI magnet and acquiring magnetic resonance signals from an object moved into an MRI signal acquisition region within and surrounded by the cylindrical static Mill magnet, the object being arranged to be moved from a bed located on a first side of the acquisition region into the acquisition region by moving at least part of the bed towards an opposite second side of the acquisition region;
    a magnetic field adjustment structure placed and configured to improve flail uniformity of the static magnetic field formed in a magnetically shielded room in which the cylindrical static Mill magnet is placed, the magnetic field adjustment structure being placed outside the magnet, and
    wherein said magnetic field adjustment structure is placed outside the acquisition region on at least one of said sides.

11. The magnetic resonance imaging apparatus of claim 10,
    wherein said magnetic field adjustment structure includes a ferromagnetic substance, the ferromagnetic substance being an element of the bed.

12. The magnetic resonance imaging apparatus of claim 10, wherein said magnetic field adjustment structure includes a ferromagnetic substance on the bed.

13. The magnetic resonance imaging apparatus of claim 10,
wherein said magnetic field adjustment structure comprises:
a coil configured to improve uniformity of the static magnetic field, the coil being placed on the second side and outside the acquisition region; and
a ferromagnetic substance placed to the bed or in the bed side, said ferromagnetic substance being a part of the bed or a part added to the bed.

14. The magnetic resonance imaging apparatus of claim 10,
wherein said magnetic field adjustment structure include a ferromagnetic substance whose height is changed with a top plate of the bed so as to improve uniformity of the static magnetic field by said ferromagnetic substance when a height of the top plate has become a height for sending the top plate into the acquisition region.

15. The magnetic resonance imaging apparatus of claim 10,
wherein said magnetic field adjustment structure has a ferromagnetic substance placed to the bed or on the first side, said ferromagnetic substance being a part of the bed or a part added to the bed, the bed being configured to move a top plate with a larger torque than a magnetic force attracting the ferromagnetic substance to the magnet.

16. A method of adjusting a magnetic field for a magnetic resonance imaging (MM) apparatus comprising:
arranging a magnetic field adjustment structure outside a cylindrical static MM magnet of the MRI apparatus, the cylindrical static Mill magnet surrounding an Mill signal acquisition region, and a bed of the MRI apparatus located on a first side of the acquisition region with at least a part of the bed being arranged to be moved into the acquisition region towards an opposite second side of the acquisition region, wherein the magnetic field adjustment structure is placed outside the acquisition region on at least one of said sides; and improving uniformity of a static magnetic field by placing the magnetic field adjustment structure outside the acquisition region on at least one of said sides, the static magnetic field being formed by the cylindrical static Mill magnet in a magnetically shielded room.

17. A magnetic resonance imaging (MRI) method comprising:

performing a magnetic resonance imaging by forming a static magnetic field with a cylindrical static Mill magnet and acquiring magnetic resonance signals from an object moved into an MRI signal acquisition region surrounded by-the cylindrical static MM magnet, a bed located on a first side of the acquisition region with at least a part of the bed being arranged to be moved into the acquisition region towards an opposite second side of the acquisition region; and arranging a magnetic field adjustment structure outside the cylindrical static Mill magnet to improve uniformity of the static magnetic field by placing the magnetic field adjustment structure outside the acquisition region on at least one of said sides, the static magnetic field being formed by the cylindrical static Mill magnet located in a magnetically shielded room.

\* \* \* \* \*